United States Patent

Hatfield et al.

Patent Number: 6,102,864
Date of Patent: Aug. 15, 2000

[54] THREE-DIMENSIONAL ULTRASOUND IMAGING OF VELOCITY AND POWER DATA USING AVERAGE OR MEDIAN PIXEL PROJECTIONS

[75] Inventors: William Thomas Hatfield, Schenectady; Kai Erik Thomenius, Clifton Park, both of N.Y.; Anne Lindsay Hall, New Berlin, Wis.; Todd Michael Tillman, W. Milwaukee, Wis.; Patricia Ann Schubert, Milwaukee, Wis.

[73] Assignee: General Electric Company, Schnectady, N.Y.

[21] Appl. No.: 09/197,787

[22] Filed: Nov. 23, 1998

Related U.S. Application Data

[63] Continuation-in-part of application No. 08/852,613, May 7, 1997.

[51] Int. Cl.⁷ .................................................. A61B 8/00
[52] U.S. Cl. ............................................................ 600/454
[58] Field of Search ................................... 600/454, 443, 600/444, 447, 448, 446, 455; 128/916

[56] References Cited

U.S. PATENT DOCUMENTS

| | | | |
|---|---|---|---|
| 5,226,113 | 7/1993 | Cline et al. | 395/124 |
| 5,282,471 | 2/1994 | Sato | 128/660.07 |
| 5,329,929 | 7/1994 | Sato et al. | 128/916 |
| 5,365,929 | 11/1994 | Peterson | 128/661.1 |
| 5,474,073 | 12/1995 | Schwartz et al. | 600/454 |
| 5,485,842 | 1/1996 | Quistgaard | 128/660.07 |
| 5,582,173 | 12/1996 | Li | 128/660.07 |
| 5,655,535 | 8/1997 | Friemel et al. | 128/660.07 |
| 5,720,291 | 2/1998 | Schwartz | 128/661.1 |
| 5,904,653 | 5/1999 | Hatfield et al. | 600/454 |

FOREIGN PATENT DOCUMENTS 09700482   1/1997   WIPO .

*Primary Examiner*—Marvin M. Lateef
*Assistant Examiner*—Maolin Patel
*Attorney, Agent, or Firm*—Marvin Snyder; Douglas E. Stoner

[57] ABSTRACT

A three-dimensional image of flowing fluid or moving tissue using velocity or power Doppler data is displayed by using an ultrasound scanner that collects velocity or power data in a cine memory to form a volume of pixel data. Average or median pixel values are projected on an image plane by casting rays through the data volume. As the ray passes through each scan plane, a data value is assigned to the ray at that point. At each scan plane, the assigned pixel data value is tested to see if it exceeds a noise threshold. For a given ray, pixel data values above the detection threshold are accumulated until a pixel data value falls below the detection threshold. A minimum number of pixel data values exceeding the threshold are required for each ray before the average of the accumulated values is processed and/or the median value is selected. When all pixels along a given ray have been tested, the projection is complete and the average or median projection is then displayed. Uniformity within the projected image and the sharpness of edges are enhanced by projecting average or median pixel values instead of maximum pixel values.

26 Claims, 8 Drawing Sheets

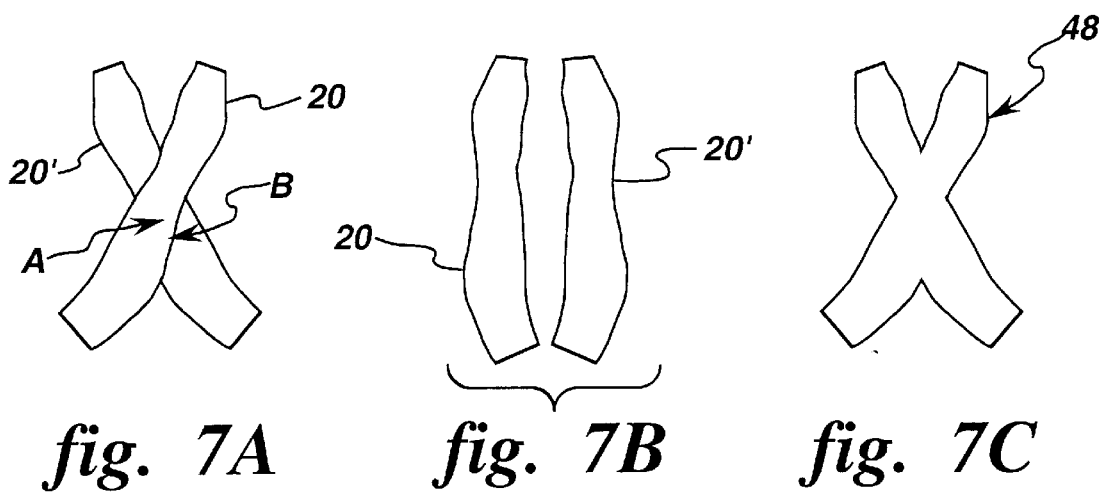
*fig. 7A*   *fig. 7B*   *fig. 7C*
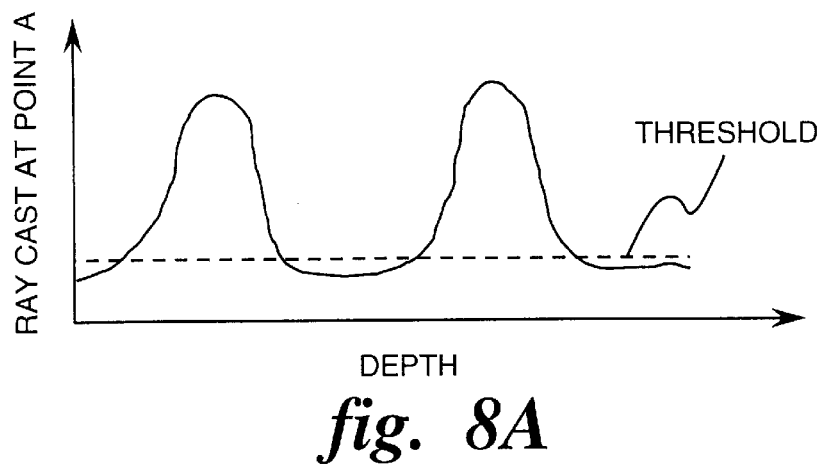
*fig. 8A*
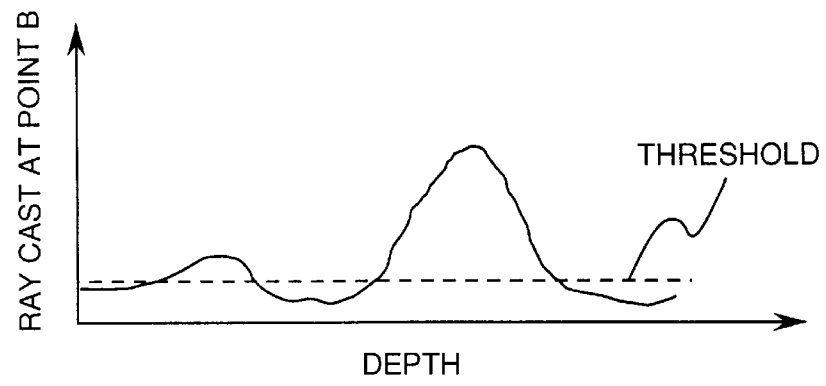
*fig. 8B*

_(6,102,864)_

THREE-DIMENSIONAL ULTRASOUND IMAGING OF VELOCITY AND POWER DATA USING AVERAGE OR MEDIAN PIXEL PROJECTIONS

RELATED PATENT APPLICATION

This application is a continuation-in-part application of U.S. patent application Ser. No. 08/852,613, filed on May 7, 1997 and assigned to the instant assignee.

FIELD OF THE INVENTION

This invention relates to anatomical ultrasound imaging for the purpose of medical diagnosis and, more particularly, to a method and apparatus for three-dimensional imaging of moving fluid or tissue in a living body by detecting Doppler shifts of ultrasonic echoes reflected from the moving fluid or tissue.

BACKGROUND OF THE INVENTION

Ultrasonic scanners for detecting blood flow based on the Doppler effect are well known. Such systems operate by actuating an ultrasonic transducer array to transmit ultrasonic waves into a body and receiving ultrasonic echoes backscattered from the body. In the measurement of blood flow characteristics, returning ultrasonic waves are compared to a frequency reference to determine the frequency shift imparted to the returning waves by flowing scatterers such as blood cells. This frequency shift, i.e., phase shift, translates into the velocity of the blood flow. The blood velocity is calculated by measuring the phase shift from firing to firing at a specific range gate.

The change or shift in backscattered frequency increases when blood flows toward the transducer and decreases when blood flows away from the transducer. Color flow images are produced by superimposing a color image of the velocity of moving material, such as blood, over a black and white anatomical B-mode image. Typically, color flow mode displays hundreds of adjacent sample volumes simultaneously, all laid over a B-mode image and color-coded to represent each sample volume's velocity.

In standard color flow processing, a high pass filter, known as a wall filter, is applied to the data before a color flow estimate is made. The purpose of this filter is to remove signal components produced by tissue surrounding the blood flow of interest. If these signal components are not removed, the resulting velocity estimate will be a combination of the velocities from the blood flow and the surrounding, non-flowing tissue. The backscatter component from non-flowing tissue is many times larger than that from blood, so the velocity estimate will most likely be more representative of the non-flowing tissue, rather than the blood flow. In order to obtain the flow velocity, the non-flowing tissue signal must be filtered out.

In a conventional ultrasound imaging system operating in the color flow mode, an ultrasound transducer array is activated to transmit a series of multi-cycle (typically 4–8 cycles) tone bursts which are focused at a common transmit focal position with common transmit characteristics. These tone bursts are fired at a pulse repetition frequency (PRF) that is typically in the kilohertz range. A series of transmit firings focused at a common transmit focal position with common transmit characteristics is referred to as a "packet". Each transmit beam propagates through the object being scanned and is reflected by ultrasound scatterers such as blood cells. The return signals are detected by the elements of the transducer array and formed into a receive beam by a beamformer.

For example, the traditional color firing sequence is a series of firings (e.g., tone bursts) along a common position, producing the respective receive signals:

$$F_1\ F_2\ F_3\ F_4\ \ldots\ F_N$$

where $F_i$ is the receive signal for the i-th firing and N is the number of firings in a packet. These receive signals are loaded into a corner turner memory, and a high pass filter (wall filter) is applied to each downrange position across firings, i.e., in "slow time". In the simplest case of a (1, −1) wall filter, each range point is filtered to produce the respective difference signals:

$$(F_1-F_2)\ (F_2-F_3)\ (F_3-F_4)\ \ldots\ (FN_{N-1}-F_N)$$

and these differences are supplied to a color flow velocity estimator.

One of the advantages of Doppler ultrasound is that it can provide noninvasive and quantitative measurements of blood flow in vessels. Given the angle $\theta$ between the insonifying beam and the flow axis, the magnitude of the velocity vector can be determined by the standard Doppler equation:

$$v = cf_d/(2f_0 \cos\theta) \quad (1)$$

where c is the speed of sound in blood, $f_0$ is the transmit frequency and $f_d$ is the motion-induced Doppler frequency shift in the backscattered ultrasound.

A conventional ultrasound imaging system collects B-mode or color flow mode images in a cine memory on a continuous basis. The cine memory provides resident digital image storage for single image review and multiple image loop review, and various control functions. The region of interest displayed during single-image cine replay is that used during the image acquisition.

If an ultrasound probe is swept over an area of interest, two-dimensional images may be accumulated to form a three-dimensional data volume. The data in this volume may be manipulated in a number of ways, including volume rendering and surface projections. In particular, three-dimensional images of power and velocity data have been formed by projecting the maximum pixel values onto an imaging plane. In this process, noise is introduced due to inherent error in estimating the velocity of power level because of a multiplicity of small scatterers present in most body fluids (e.g., red cells in blood). Noise present in the velocity and power signals causes errors in selection of the maximum value and affects uniformity within the projected image and sharpness of edges. Thus, there is need for a method for improving the uniformity and edge sharpness of three-dimensional images of velocity and power data.

SUMMARY OF THE INVENTION

In a system for displaying a three-dimensional image of flowing fluid or moving tissue using velocity or power Doppler data, an ultrasound scanner collects velocity or power data in a cine memory to form a volume of pixel data. To form a three-dimensional image, pixel values are projected on an image plane by casting rays through the data volume. As the ray passes through each scan plane, a data value is assigned to the ray at that point. This can be done by one of a number of well-known sampling algorithms, such as nearest neighbor sampling or bilinear or trilinear interpolation. At each scan plane in the data volume, the assigned pixel data value is tested to see if it exceeds a predetermined detection threshold. The threshold value is selected to reject echoes produced by background clutter. For a given ray, pixel data values above the detection threshold are accumulated until a pixel data value lower than the detection threshold is detected. As a further aid in noise rejection, for each ray a minimum number of pixel data values exceeding the threshold is required before the average of the accumulated values is processed and/or the median value is selected. This process is repeated until all pixels along a given ray have been tested. For each string of successive pixel data values exceeding the detection threshold, the computed average value or the discriminated median value is compared to the saved value and substituted for the saved value if a further criterion is met, namely, if the new value exceeds the saved value, in the case of a projection of a maximum of the average or median values acquired, or if the new value is less than the saved value, in the case of a projection of a minimum of the average or median values acquired. A final average or median value is acquired for each ray. Once the projection is complete (i.e., all rays have been tested), the average or median projection is then displayed. The uniformity within the projected image and the sharpness of edges are enhanced by projecting average or median pixel values instead of maximum pixel values.

In accordance with another preferred embodiment of the invention, both average and median values are computed and stored. Once the projection is complete, a selected one of the saved average and median values can be displayed for each pixel, so that the projected image is the result of a combination of average and median values. Where the saved average and median values are the respective maxima of the values computed for respective strings of successive pixel data values exceeding the detection threshold, the larger of the saved average and median values can be displayed. Alternatively, where the saved average and median values are the respective minima of the values computed for respective strings of successive pixel data values exceeding the detection threshold, the smaller of the saved average and median values can be displayed.

BRIEF DESCRIPTION OF THE DRAWINGS

FIGS. 7A and 7B are schematic front and side views of overlapping vessels.

FIG. 7C is a schematic 0-degree average pixel projection of the overlapping vessels shown in FIG. 7A.

FIGS. 8A and 8B are graphs showing data values as a function of depth for two rays cast at respective points A and B shown in FIG. 7A.

DETAILED DESCRIPTION OF THE PREFERRED EMBODIMENTS

Figure 1:
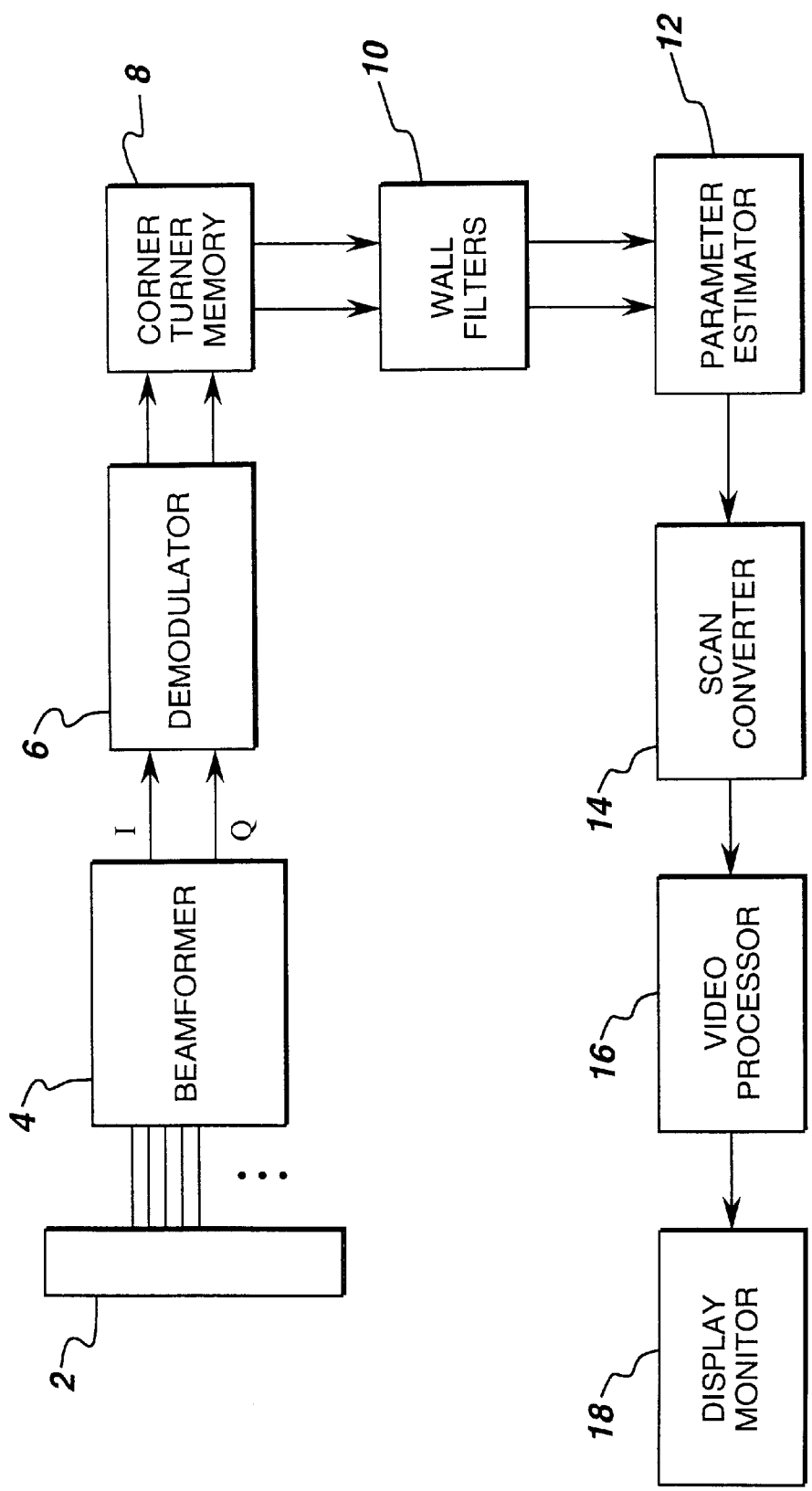
FIG. 1 is a block diagram of the major functional subsystems within a real-time ultrasound imaging system.

The basic signal processing chain for a color flow imaging system, shown in FIG. 1, comprises an ultrasound transducer array 2 that is activated to transmit coded pulse sequences comprising phase-coded tone bursts of length P fired repeatedly at the PRF. The return RF signals are detected by the transducer elements and received by respective receive channels in a beamformer 4 that sums the delayed channels data and supplies either RF or in-phase and quadrature (IIQ) data. The latter alternative is illustrated in FIG. 1.

In a conventional system, the beamformer output signal frequencies are shifted to baseband by a demodulator 6. The demodulated IIQ components are stored in a corner turner memory 8, whose purpose is to buffer data from possibly interleaved firings and supply the data as vectors of points across firings at a given range cell. Data are received in "fast time", or sequentially downrange (along a vector) for each firing. The output signal of the corner turner memory is reordered into "slow time", or sequentially by firing for each range cell. The resultant "slow time" IIQ signal samples are passed through respective wall filters 10, which reject any clutter corresponding to stationary or very slow-moving tissue. The filtered output signals are supplied to a parameter estimator 12 which converts the range cell information into the intermediate autocorrelation parameters N, D, and R(0). N and D are the numerator and denominator for the autocorrelation equation, as shown below:

$$N = \sum_{i=1}^{M-1} (I_i Q_{i+1} - I_{i+1} Q_i) \quad (2)$$

$$D = \sum_{i=1}^{M-1} (I_i I_{i+1} + Q_i Q_{i+1}) \quad (3)$$

where $I_i$ and $Q_i$ are the demodulated, basebanded input data for firing i, and M is the number of firings in the packet. R(0) is approximated as a finite sum over the number of firings in a packet, as follows:

A processor converts N and D into a magnitude and phase for each range cell. The equations used are:

$$R(0) = \sum_{i=1}^{M-1} \frac{I_i^2 + Q_i^2 + I_{i+1}^2 + Q_{i+1}^2}{2} \quad (4)$$

$$|R(T)| = \sqrt{N^2 + D^2} \quad (5)$$

$$\phi(R(T)) = \tan^{-1}\left[\frac{N}{D}\right] \quad (6)$$

The parameter estimator processes the magnitude and phase values into estimates of power, velocity and turbulence. The phase is used to calculate the mean Doppler frequency, which is proportional to the velocity (as shown below). R(0) and |R(T)| are used to estimate the turbulence.

The mean Doppler frequency in hertz is obtained from the phase of N and D and the pulse repetition time T:

$$\overline{f} = \frac{1}{2\pi T}\tan^{-1}\left[\frac{N}{D}\right] = \frac{1}{2\pi T}(\phi(R(T))) \quad (7)$$

The mean velocity is calculated using the Doppler shift equation below. Since θ, the angle between the flow direction and the sampling direction, is not known, cos θ is assumed to be 1.0.

$$\overline{v} = \frac{\overline{f}}{f_0}\frac{c}{2\cos\theta} \quad (8)$$

The parameter estimator does not calculate the mean Doppler frequency as an intermediate output signal, but calculates $\overline{v}$ directly from the phase output of the processor using a look-up table.

The turbulence may be calculated in the time domain as a second-order series expansion of the variance of the mean Doppler frequency. The time domain expression for turbulence involves calculating the zero-lag and one-lag autocorrelation functions, R(0) and R(T) respectively. The exact autocorrelation functions are approximated by finite sums over the known data in the number of firings in a packet:

$$\sigma^2 = \frac{2}{(2\pi T^2)}\left[1 - \frac{|R(T)|}{R(0)}\right] \quad (9)$$

The mean value signal φ(R(T)) is an estimate of the mean Doppler frequency shift of the flowing reflectors, which in turn is proportional to the mean blood flow velocity. The variance signal $\sigma^2$ indicates the frequency spread of the flow signal component of the baseband echo signal. This value is indicative of flow turbulence, since laminar flow has a very narrow range of velocities, while turbulent flow is a mixture of many velocities. To indicate the strength of the signal from the flowing reflectors, signal R(0) indicates the amount of the returned power in the Doppler-shifted flow signal.

The color estimates are sent to a scan converter 14, which converts the color images into X—Y format for video display. The scan-converted frames are passed to a video processor 16, which basically maps the scan-converted data to a display color map for video display. The color flow image frames are then sent to a video monitor 18 for display. Typically, either velocity or power is displayed alone or velocity is displayed in conjunction with either power or turbulence. System control is centered in a host computer (not shown), which accepts operator inputs through an operator interface (e.g., a keyboard) and in turn controls the various subsystems.

Figure 2:
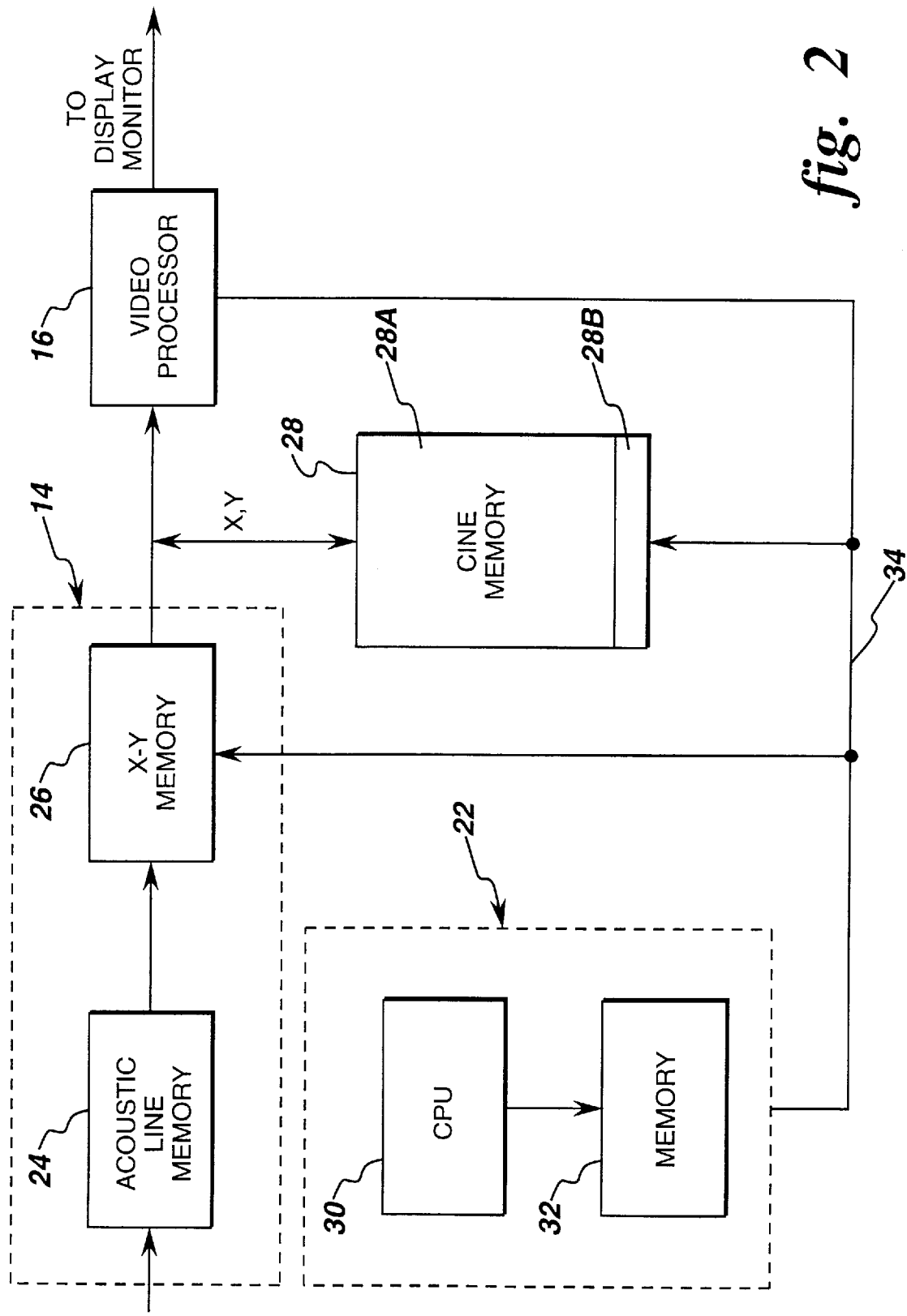
FIG. 2 is a block diagram of the means for constructing frames comprising successive volumetric projections of pixel intensity data.

As shown in FIG. 2, system control is centered in a master controller or host computer 22, which accepts operator inputs through an operator interface (not shown) and in turn controls the various subsystems. The master controller also generates the system timing and control signals. Scan converter 14 comprises an acoustic line memory 24 and an X—Y memory 26. The color data stored in acoustic line memory 24 is transformed to appropriately scaled Cartesian coordinate display color data, which are stored in X—Y memory 26. A multiplicity of successive frames of color data are stored in a cine memory 28 on a first-in, first-out basis. The cine memory is similar to a circular image buffer that runs in the background, continually capturing image data that are displayed in real time to the user. When the user freezes the system, the user has the capability to view image data previously captured in cine memory 28.

Host computer 22 comprises a processor or central processing unit (CPU) 30 and a random access memory 32. CPU 30 has random access memory incorporated therein for storing routines used in transforming an acquired volume of intensity data into a multiplicity of three-dimensional projection images taken at different angles. CPU 30 controls X—Y memory 26 and cine memory 28 via a system control bus 34. In particular, CPU 30 controls the flow of data from X—Y memory 26 to video processor 16 and to cine memory 28, and from the cine memory to video processor 16 and to CPU 30 itself. Each frame of imaging data, representing one of a multiplicity of scans or slices through the body being examined, is stored in X—Y memory 26 and in the next cycle is transmitted to video processor 16 and to cine memory 28. A stack of frames, representing the scanned body volume is stored in a section 28A of cine memory 28.

A conventional ultrasound imaging system collects B-mode or color flow mode images in a cine memory on a continuous basis. The cine memory provides resident digital image storage for single image review and multiple image loop review, and various control functions. The region of interest displayed during single-image cine replay is that used during the image acquisition. The cine memory also acts as a buffer for transfer of images to digital archival devices (not shown) via host computer 22.

If an ultrasound probe is swept over an area of interest, two-dimensional images may be accumulated to form a three-dimensional data volume. The data in this volume may be manipulated in a number of ways, including volume rendering and surface projections. In the process of forming three-dimensional images of power and velocity data by projecting the maximum pixel values onto an imaging plane, noise is introduced due to inherent error in estimating the velocity or power level because of a multiplicity of small scatterers present in most body fluids (e.g., red cells in blood). Noise present in the velocity and power signals causes errors in selection of the maximum value and affects uniformity within the projected image and sharpness of edges.

CPU 30 contains random access memory for storing routines used in transforming an acquired volume of velocity or power data into a multiplicity of three-dimensional projection images taken at different angles. CPU 30 controls X—Y memory 26 and cine memory 28 via system control bus 34. In particular, CPU 30 controls the flow of data from acoustic line memory 24 or X—Y memory 26 of scan converter 14 to video processor 16 and to cine memory 28, and from the cine memory to the video processor and to the CPU itself. Each frame of velocity data, representing one of a multiplicity of scans or slices through the body being examined, is stored in X—Y memory 26 and in the next cycle is transmitted to video processor 16 and cine memory 28. A stack of frames, representing the scanned body volume, is stored in section 28A of cine memory 28. In response to initialization (step 36 in FIG. 3), CPU 30 retrieves from cine memory section 28A only the velocity or power data corresponding to a body volume of interest. This is accomplished by retrieving only the velocity or power data in a region of interest from each selected frame. The data corresponding to the region of interest from each one of a multiplicity of selected frames form a source data volume of interest, which is stored in local memory (step 38 in FIG. 3).

In accordance with a preferred embodiment of the invention, the source data volume of interest comprises those pixels having a velocity or power component within a predetermined range, e.g., having non-zero values. The velocity or power data in the source data volume are then used to construct projected images taken at different viewing angles.

The velocity or power projections are constructed in CPU 30, which performs a series of transformations using the ray-casting algorithm disclosed in U.S. Pat. No. 5,226,113, issued Jul. 6, 1993 and assigned to the instant assignee. The successive transformations represent average or median projections made at angular increments, e.g., at 10° intervals, within a range of angles, e.g., +90° to −90°. However, the angular increment need not be 10°, nor is the invention limited to any particular range of angles.

Figure 4:
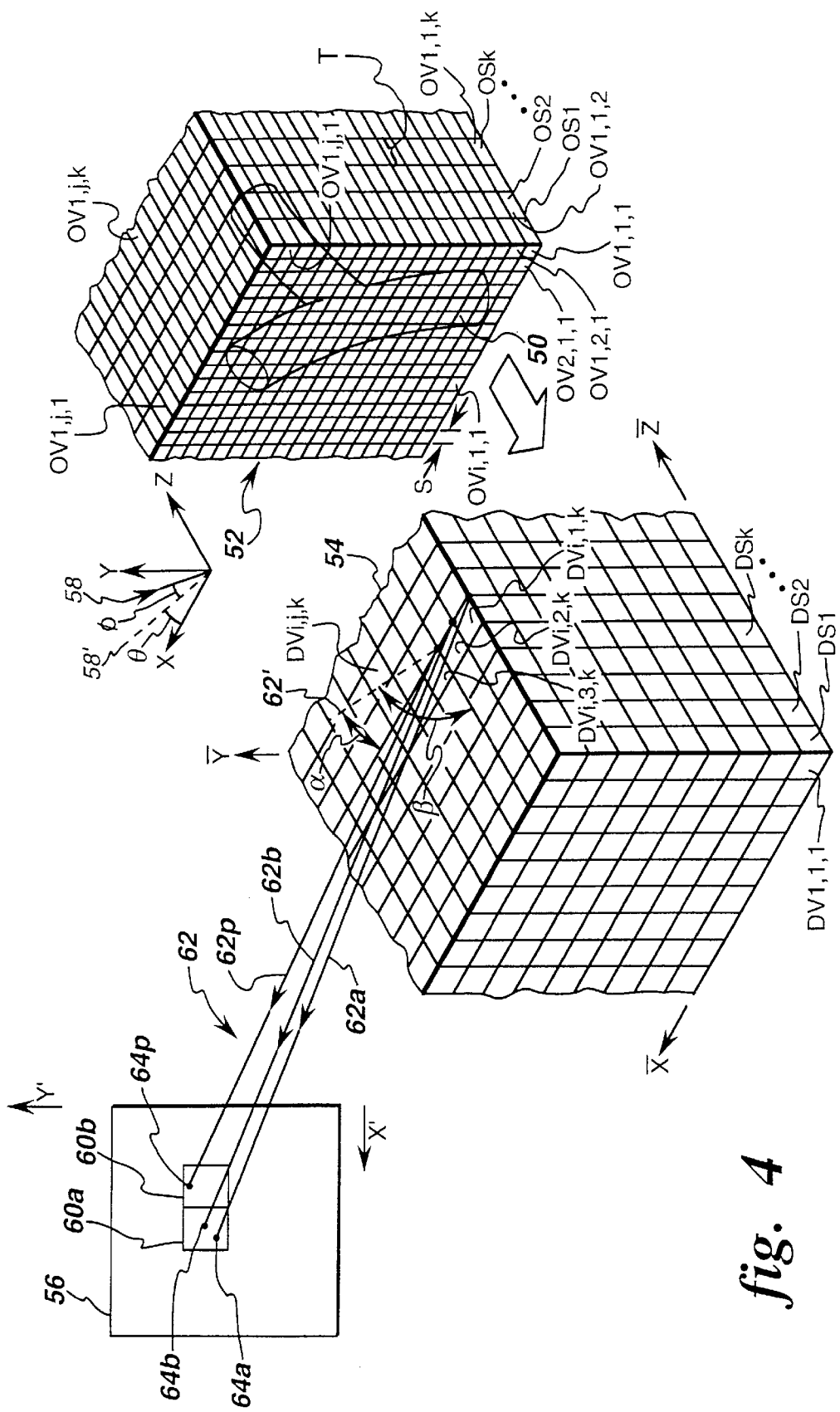
FIG. 4 is a schematic illustration of the sampled object volume of interest, an associated data volume and an image projection plane involved in volumetrically rendering a reversed ray-cast projection.

In accordance with the ray casting technique employed in the present invention, a volumetrically rendered projection image of a sample 50 (see FIG. 4) is displayed from any arbitrary viewing angle, e.g. a spherical projection angle denoted by angle parameters $(\theta,\phi)$, where $\theta$ is the angle that an extension 58' of a viewing ray 58 makes upon the XY plane, and $\phi$ is the angle of ray 58 with respect to extension 58', by scanning an object (body) volume 52 with an ultrasound transducer. Sample volume 52 is scanned in such a manner as to create a series of stacked, contiguous slices or sheets $OS_1, OS_2, \ldots, OS_k$, each of which contains the same number of object volume elements (voxels) OV. Each voxel has a rectangular profile in the sheet plane (say, the XY plane), while the complementary sides may be of equal length S, so that this profile may be square. The sheet thickness T is generally not equal to the length of either side. Thus, the first object slice $OS_1$ contains a first multiplicity of object voxels $OV_{i,j,1}$, where i and j are the respective X-axis and Y-axis positions of the voxel. Similarly, the second object slice $OS_2$ contains object voxels $OV_{i,j,2}$. An arbitrary object slice $OS_k$ contains voxels $OV_{i,j,k}$, where k is the Z-axis position of that voxel.

Each object voxel $OV_{i,j,k}$ is analyzed and the data value (velocity or power) thereof is placed in a corresponding data voxel $DV_{i,j,k}$ of a data volume 54. Data volume 54 is a simple cubic i,j,k lattice, even though the thickness of each object slice $OS_k$ and each object voxel face size (the size of the voxel in the XY plane) will generally not be the same. That is, not only may the object volume have different X, Y and Z dimensions for each voxel, but also the total number of voxels in any dimension need not be the same. For example, a typical ultrasound three-dimensional scan may provide each slice with a 256×256 matrix of voxels, and may involve 128 slices.

In accordance with a known technique employed by CPU 30, an image of object 50 is projected (step 42 in FIG. 3) by ray casting toward image plane 56 from a lattice point in data voxel $DV_{i,j,k}$. For convenience, the lattice point may, for example, be the data voxel vertex closest to the data volume origin. The cast ray 62 leaves data volume 54 at a projection angle with spherical angular parameters $(\alpha,\beta)$ transformed from the spherical angular parameters $(\theta,\phi)$ at which object volume 52 is viewed. These two angles are not the same, due to geometric distortion caused by use of a cubic data volume 54 with a non-cubic object volume 52. However, projected ray 62 has an $\bar{x}-\bar{y}$ plane extension 62' which makes an angle $\alpha$ with respect to the $\bar{x}$ axis of the data volume and an angle $\beta$ with respect to the $\bar{z}$ axis. Thus, angles $\alpha$ and $\beta$ are determined by a rotation process (discussed hereinbelow) to correspond to viewing object volume 52 at the desired viewing angle $(\theta,\phi)$ (assuming operation in spherical coordinates). Each of rays 62 is cast from the data volume voxel lattice point toward the image plane.

While all rays 62 impinge upon some portion of the image plane, only those rays falling within image plane pixel 60a under consideration are allowed to contribute to the data for that image plane pixel. Thus, having chosen a portion of object volume 52 to view and a viewing angle $(\theta,\phi)$ at which to view this selected object volume, the data value in each voxel of the corresponding portion of the data volume is cast at some angle $(\alpha, \beta,$ corresponding to viewing the distorted data volume with respect to the object volume) toward image plane 56. The data value in a first voxel (say, voxel $DV_{i,1,k}$) is thus back-projected along ray 62a, in accordance with the $\theta$ and $\phi$ values chosen. Ray 62a impinges upon image plane 56 at a position 64a within pixel 60a, and, as this is the first ray to impinge upon this pixel, the velocity or power value of the incident data is attributed to (stored in) the desired pixel 60a. The next voxel in the data volume (say voxel $DV_{i,2,k}$) has its associated ray 62b projected at the same angular $(\alpha, \beta)$ configuration from the voxel lattice point, and its position 64b upon image plane 56 is noted. Assuming that impingement position 64b is within desired pixel 60a, the second projected value is added to the first projected value. For an averaged-value projection, the value of a current projected data voxel is added to the sum already stored for the image panel pixel upon which that projection ray impinges, and the sum is eventually divided by a counted number of such impinging rays for that pixel. As each voxel in the selected data volume is sequentially entered and projected toward image plane 56, a data volume voxel (say, voxel $DV_{i,3,k}$) is eventually projected along its associated ray 62p and does not impinge within the desired pixel 60a, so that its data value is not added to the summed value presently stored for pixel 60a. The average data value for pixel 60a is then computed for that projection of the data at the particular $(\theta,\phi)$ three-dimensional angle of view. However, ray 62p does, in fact, have an impingement point 64p which falls within another image plane pixel (say, pixel 60b) and is added to the summed data value stored therein. All data values are reset to zero when a new projection is to be taken. Thus, each of the image plane pixels is reset at the start of an image projection procedure, and all of the data volume voxels (in the entire space or in the selected portion, as set by the portion of object volume 52 selected) are individually and sequentially scanned. The data value in each data voxel DV is projected through an associated ray 62 to impinge upon image plane 56 in one pixel 60 thereof. Then the average value, median value, or both, are computed for each pixel, and displayed.

Figure 3:
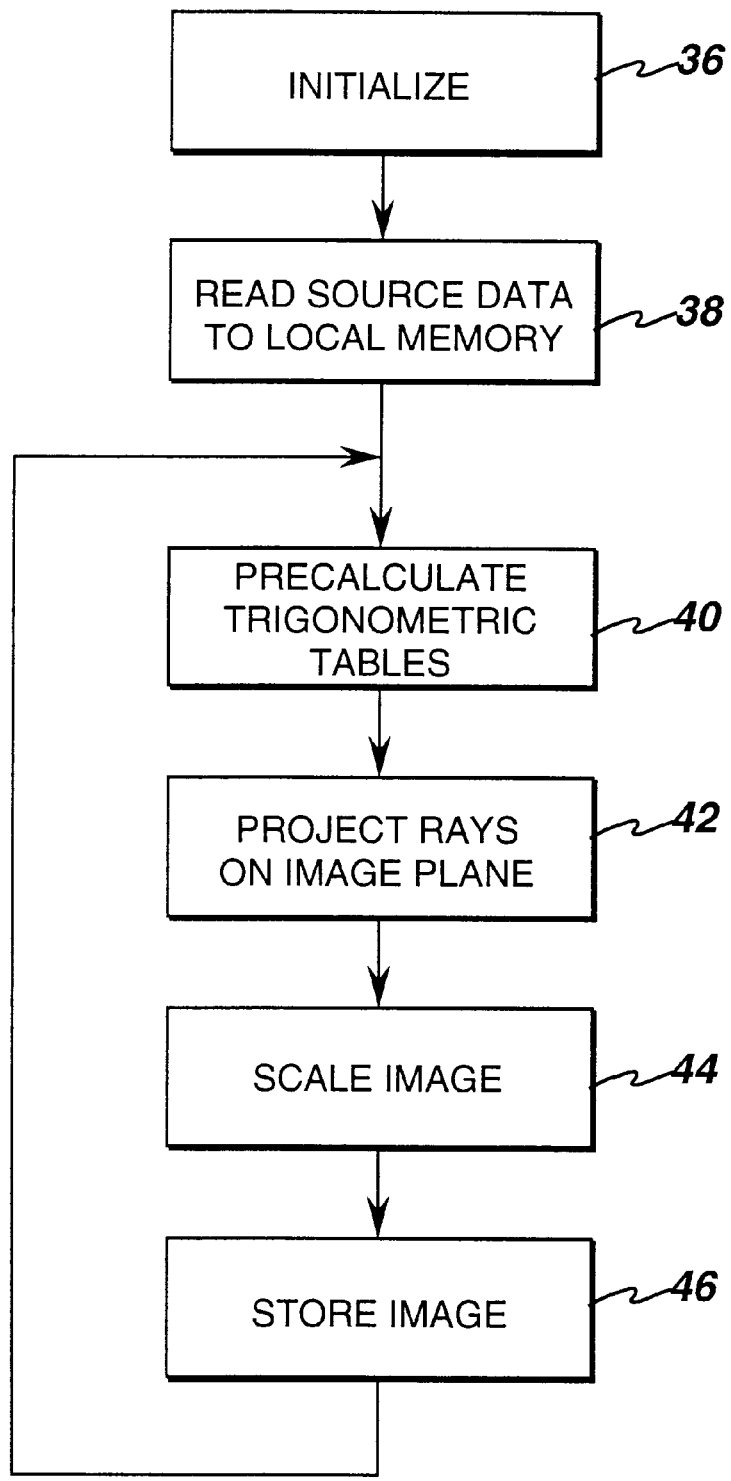
FIG. 3 is a flowchart of an algorithm for constructing frames comprising successive volumetric projections of pixel intensity data.
Figure 5:
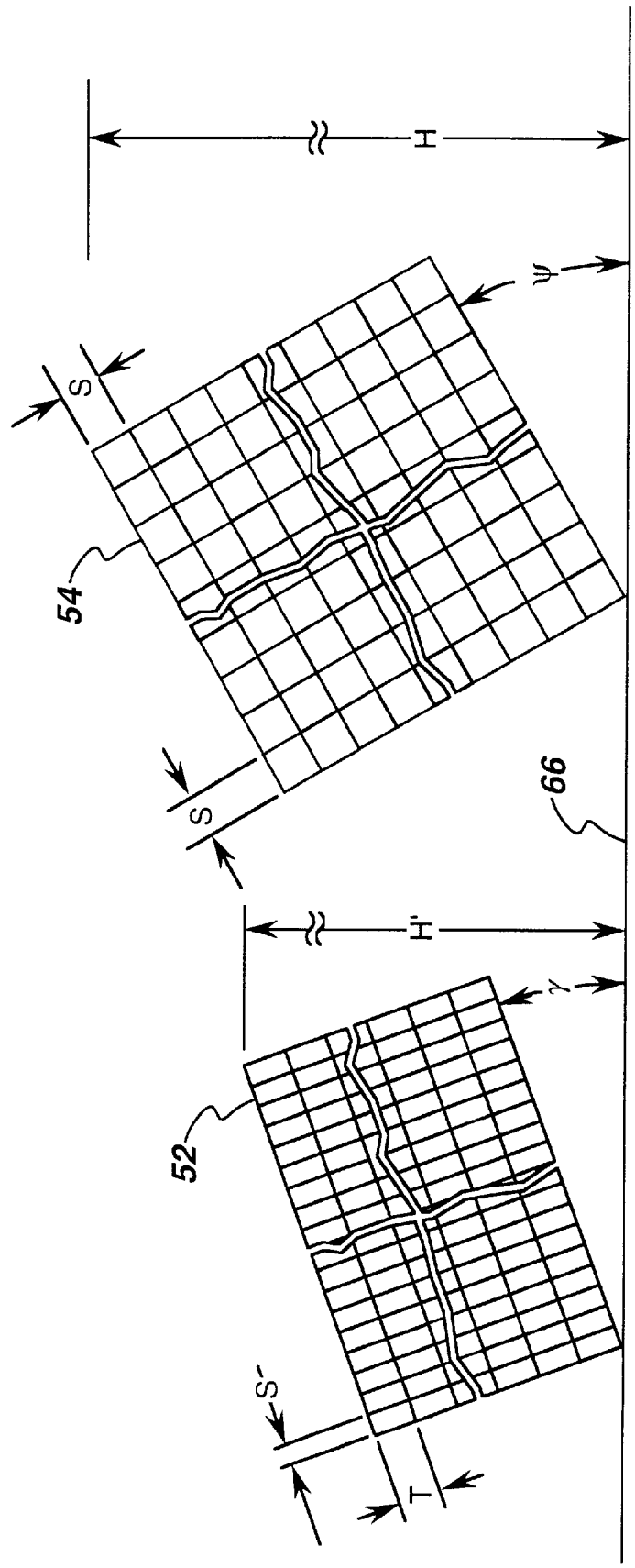
FIG. 5 is a schematic illustration of a pair of geometric two-dimensional configurations corresponding to like views of object and data volumes, and useful in defining necessary scaling constants in three-dimensional ultrasound imaging.

In accordance with another aspect of the foregoing technique, the data projection is scaled and then stored (steps 44 and 46 in FIG. 3). In scaling, any anisotropy between the object volume and the image plane is removed by only a single set of calculations after back-projection is complete. Referring now to FIG. 5, because object volume 52 is a real volume while data volume 54 is an abstract concept, it is necessary to determine the amount of distortion of the data projection due to the presentation of cubic data volume lattice 54 at a different angle $\gamma$, in a first plane, and then the angle $\psi$ at which an arbitrary viewing direction 66 will be positioned with respect to both the object volume 52 and data volume 54. The apparent dimensions of each voxel will change as the effective elevation angles $\gamma$ and $\psi$ change. If the aspect ratio A (defined as the ratio of the actual slice thickness T in object volume 52 to the actual pixel size S in the same object volume 52) is not unity (i.e., is greater or less than unity, as the object voxel is not a cubic voxel, as will be encountered in data volume 54), then the angles $\psi$ and $\gamma$ of elevation will be different, and the effective elevation angle $\psi$ in the data volume will be different than the actual elevation angle $\gamma$ in the object volume. Rotation of the data is in accordance with an object elevation angle obtained by:

$$\psi = \tan^{-1}\left(\frac{1}{A}\tan[\gamma]\right) \quad (10)$$

Thereafter, the projected data can be scaled to have the correct height (if rotation is about the horizontal axis) in the object volume, by multiplication of all projected data heights by the elevation scale factor. The old projected image height H can be corrected with an effective scale factor $E_s$, where $$E_s = \sqrt{(A\cos\gamma)^2 + \sin^2\gamma} \quad (11)$$

and the new height $H' = H \cdot E_s$. The same is true for the width when rotation is about the vertical axis.

Utilizing the above relationship, the rotation of data volume angles (α, β) becomes angles (θ, φ), because the distortion is only along one axis, so that angle θ equals angle α. The elements of the 3×3 rotational matrix [M] can be determined, and given the two involved rotational angles, these relationships are used to determine the data volume-to-image plane transformations:

$$X' = M1X + M2Y + M3Z + XO \quad (12)$$

$$Y' = M4X + M5Y + M6Z + YO \quad (13)$$

where M1–M6 are the first two rows of the rotational matrix (i.e., M1=−sin θ, M2=cos θ sin ψ, M3=0, M4=−cos θ sin ψ2, M5=−sin θ sin ψ, and M6=cos ψ), X' and Y' are the locations on the image plane of the projected point, and XO and YO are image plane X and Y offsets (respectively referenced to the X and Y lowest value points) at which the selected portion of the image plane begins. After the data are projected onto image plane 56, the image is scaled to correct for the effect of the anisotropic object voxels. It will be seen that factors M1–M6 can be precalculated (step 40 in FIG. 3) at the beginning of a projection (given θ and φ) and used for all rotation calculations.

Figure 6:
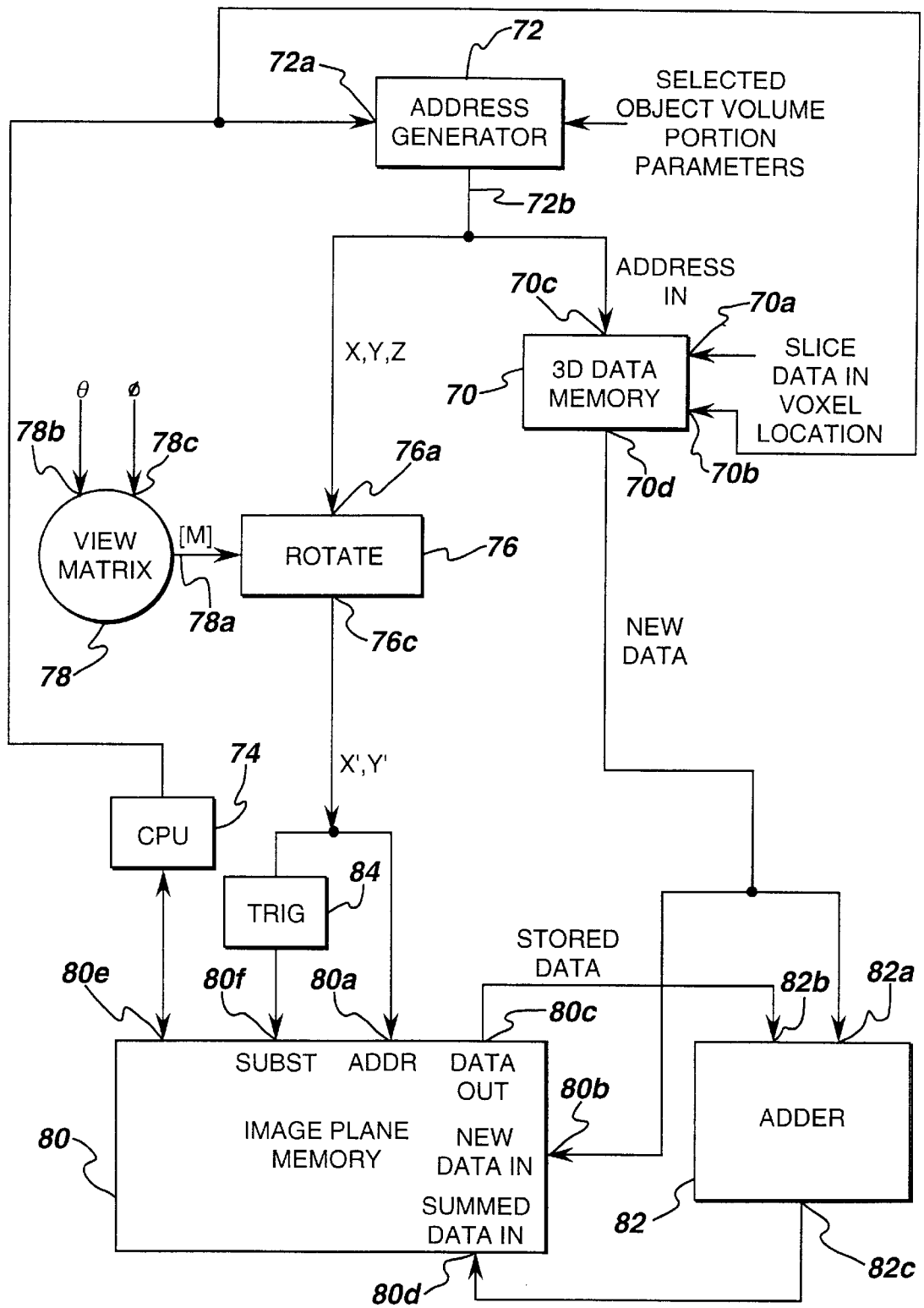
FIG. 6 is a block diagram of means for providing an average pixel intensity projection in accordance with one preferred embodiment of the invention.

FIG. 6 shows means for performing the above-described ray-casting technique which are incorporated in the host computer and comprise a three-dimensional data memory 70 for storing slice data as received at a data input 70a from cine memory 28 (FIG. 2). The data associated with each object voxel are stored at the address of that voxel, responsive to voxel address input information received at a voxel address input 70b from a CPU 74. When the data memory is filled (corresponding to the transfer of all required data from object volume 52 to data volume 54), the object volume portion of interest is selected and data establishing its starting corner and extent in the X, Y and Z directions are sent from CPU 74 to an input 72a of an address generator 72 which sequentially provides, at an address output 72b, the X,Y,Z addresses of each voxel within the object volume selected. Address output 72b is connected to an output-data-address input 70c of data memory 70, causing the stored intensity data for that one voxel then addressed to be produced at data memory means output 70d. The sequence of voxel X,Y,Z addresses is also provided to a first input 76a of a rotational parameter calculator 76, which receives angle (α, β) information via CPU 74 as the calculated matrix element M1–M6 values, to provide at an output 76c the address X',Y' of the image plane pixel corresponding to that object X,Y,Z pixel when viewed at a selected viewing angle (θ, φ). The viewing angle (θ, φ) information is entered into the system and processed by CPU 74. The results are entered into inputs 78b and 78c of a viewing matrix 78, to provide matrix elements M1–M6 at its output 78a and thence to rotational parameter calculator 76.

In accordance with a preferred embodiment of the invention, the average intensity of each image plane pixel is found by the following methodology. For each object volume voxel address X,Y,Z, new data are applied to data input 82a of an adder 82. Simultaneously, the rotated address appears as to corresponding image plane address X',Y' at the address input 80a of an image plane memory 80. The appearance of new address data is sensed by a trigger 84, to provide a substitute-data signal at input 80b. This signal occurs with sufficient delay so that data previously stored at that address in image plane memory 80 are retrieved and applied to data input 82b of adder 82 via data output 80c of image plane memory 80. The adder forms the sum of the new and stored data and makes that sum available at its output 82c, which is connected to the summed data input 80d of image plane memory 80. The summed data are stored at address X',Y' in image plane memory 80, for that pixel of the image plane, until all of the object volume voxels in the volume of interest have been scanned, and have made their contribution to the associated pixels of the image plane. The image plane pixel sum values are then operated upon by CPU 74 via data port 80e of image plane memory 80, in accordance with the number of additions for each image plane pixel (which is a number obtained by adding activations of input 80d for each pixel and is also stored in image plane memory 80) to derive the average intensity for each image plane pixel for storage and subsequent display. In the color flow mode, the averaged pixel value represents average flow velocity and, in the power Doppler mode, the averaged pixel value represents the power contained in the returned Doppler signal.

In an alternative embodiment, median pixel projections are performed by storing respective lists of the projected values for each pixel on the image frame and then discriminating the respective median pixel value for each pixel after all of the object volume voxels in the volume of interest have been scanned. These median values are then displayed. For median pixel projections, the new data from output 70d are provided to a new data input 80f of image plane memory 80. The data values are ordered in a median table by CPU 74, which also later discriminates the median value from the values contained in the table.

In accordance with a further variation, both the average and the median values are computed and stored for each pixel projection. A selection algorithm is then applied to the average and median values for each pixel to determine which value is to be used in the projected image to be displayed. For some applications, a selection algorithm which selects the larger of the two values may be used. For other applications, a selection algorithm which selects the smaller of the two values may be used.

For applications in which the projected pixel values along a given cast ray have multiple peaks above a predetermined detection threshold, further refinement of the projection algorithm is desirable. In particular, an algorithm is needed which would prevent two vessels 20 and 20' at different depths (shown in FIG. 7B) which appear to cross each other when viewed from the front (shown in FIG. 7A) from being imaged as a single X-shaped vessel 48, as seen in FIG. 7C. FIG. 7C shows the effect of a simple average pixel projection of two overlapping vessels. To avoid an image showing one vessel having four branches, preferably a technique called "depth queuing" can be employed. FIGS. 8A and 8B show the resulting amplitudes as respective rays are cast through the volume from front to back at points A and B seen in FIG. 7A. In accordance with the depth queuing technique of the preferred embodiment, data points above the threshold are accumulated until they again fall below the threshold. As soon as the data values fall below the threshold and there are enough data points to meet a criterion for valid data, the search along that ray is terminated. Thus the first average/median packet found will be displayed.

Figure 9:
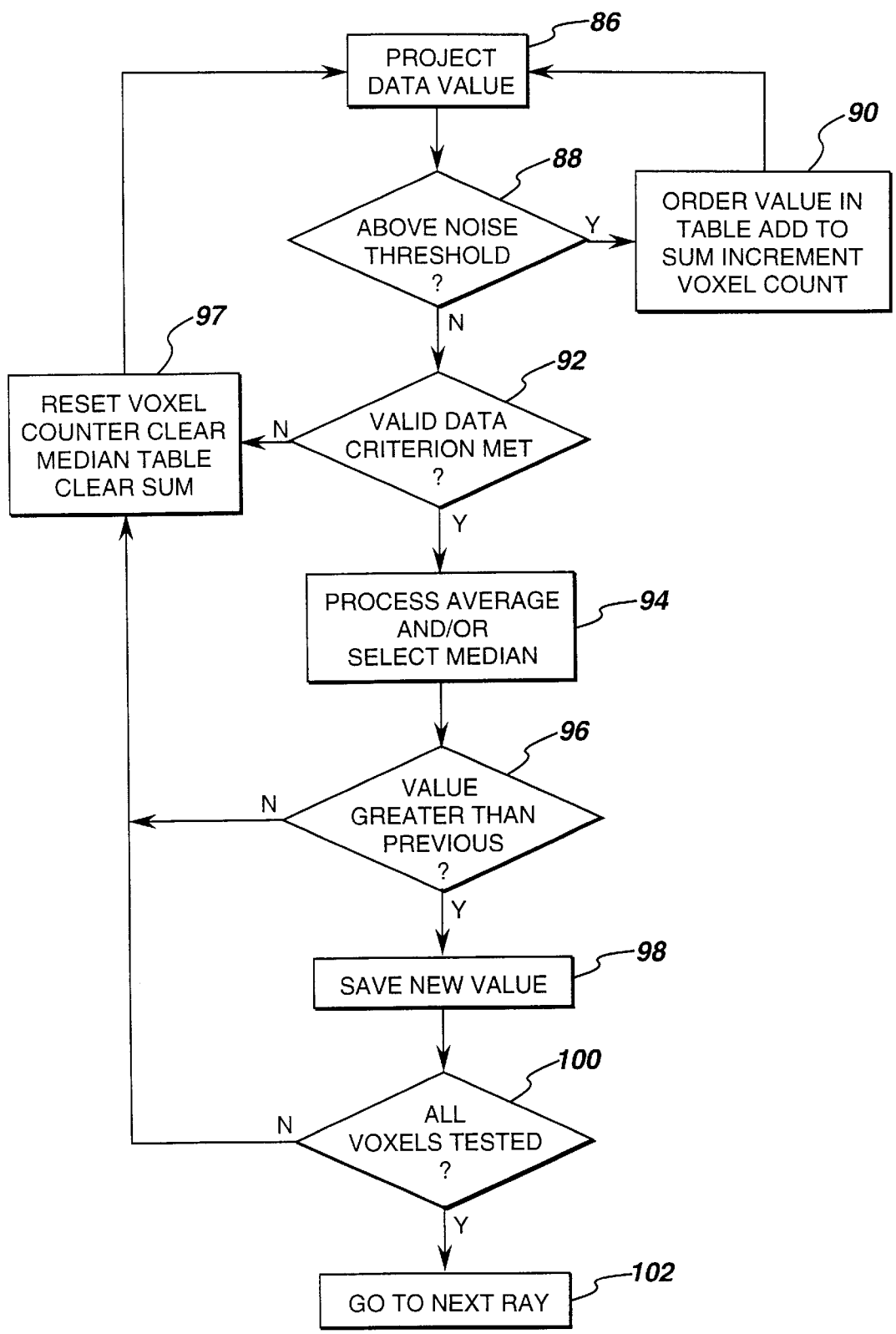
FIG. 9 is a flowchart of an algorithm for providing an average or median pixel intensity projection in accordance with preferred embodiments of the invention.

In accordance with the preferred technique depicted in FIG. 9, the data value in each data voxel is projected (step 86) through an associated ray to impinge upon an image plane in one pixel thereof. As the ray passes through each scan plane, a data value is assigned to the ray at that point. This can be done by one of a number of well-known sampling algorithms, such as nearest neighbor sampling or bilinear or trilinear interpolation. At each scan plane in the data volume, the assigned pixel data value is tested at step 88 to see if it exceeds a predetermined detection threshold. The threshold value is selected to reject echoes produced by background clutter. For a given ray, pixel data values above the detection threshold are accumulated until a pixel data value lower than the detection threshold is detected. In particular, at step 90 the respective data value is ordered in a median table and/or added to the sum of previous data values, and a voxel counter is incremented. In response to a data value below the noise threshold, a determination is made at step 92 to ascertain whether any data above the noise threshold are valid. In particular, as a further aid in noise rejection, for each ray a minimum number of pixel data values exceeding the noise threshold are required before the average of the accumulated values is processed and/or the median value is selected. If this valid data criterion is met, then the ordered values in the median table are processed to discriminate a median value and/or the summed value is divided by the voxel count at step 94 to determine an average value. The average value and/or the median value for the first string of successive pixel data values exceeding the noise threshold is saved. If the data are not valid, then the voxel counter is reset, the median table is cleared and the sum is cleared (step 97). This process is repeated until all data voxels along a given ray have been tested. At step 98, for each subsequent string of successive pixel data values exceeding the noise threshold, the computed average value and/or the discriminated median value is compared to the respective saved value and substituted for that saved value if a further criterion is met, namely, if the new value exceeds the saved value (step 96), in the case of a projection of a maximum of the average or median values acquired. (Alternatively, in the case of a projection of a minimum of the average or median values acquired, the new value is substituted for the saved value if the former is less than the latter.) A final average value and/or a final median value is acquired for each ray, at step 100, after all data voxels projected along that ray have been tested. The foregoing process is then repeated at step 102 for the next ray. When the projection is complete (i.e., all rays have been tested), either the saved average pixel values or the saved median pixel values are displayed.

In accordance with one preferred embodiment, both average and median values are both computed and stored. When the projection is complete, a selected one of the saved average and median values can be displayed for each pixel, so that the projected image is the result of a combination of average and median values. Where the saved average and median values are the respective maxima of the values computed for respective strings of successive pixel data values exceeding the detection threshold, the larger of the saved average and median values can be displayed. Alternatively, where the saved average and median values are the respective minima of the values computed for respective strings of successive pixel data values exceeding the detection threshold, the smaller of the saved average and median values can be displayed The method illustrated by the algorithm shown in FIG. 3 is applied to the velocity or power data for the data volume of interest retrieved from the cine memory. Each pixel in the projected image includes a respective transformed velocity or power datum derived by projection onto a given image plane. In addition, and with reference to FIG. 2, at the time when cine memory 28 is frozen by the operator, CPU 30 stores the last frame from X—Y memory 26 at multiple successive addresses in section 28B of the cine memory. The projected image data for the first projected view angle is written into the first address in cine memory section 28B, so that the projected image data in a region of interest is superimposed on the background frame. This process is repeated for each angular increment until all projected images are stored in cine memory section 28B, each projected image frame being comprised of a region of interest containing transformed data and, optionally, a background perimeter surrounding the region of interest and comprised of background frame data not overwritten by region-of-interest transformed data. The background image makes clearer where each displayed projection is viewed from. The operator can then select any projected image for display. In addition, the sequence of projected images can be replayed on the display monitor to depict the object volume as if it were rotating in front of the viewer.

When forming the velocity or power source data volume, two types of gating can be used to identify the frames or scans from which velocity or power data will be taken. If the system operator is interested in blood flow at some point in the patient's cardiac cycle, the system is connected to receive data from a cardiac monitor, to which the patient is connected. At each cycle, the monitor produces a signal in response to occurrence of a predetermined characteristic in the cardiac cycle waveform. In response to output signals from the monitor, the master controller stores in cine memory the frame which is present in the X—Y memory when the trigger event occurs or at a predetermined delay interval subsequent thereto. Thus, one frame per cycle is stored in cine memory. Alternatively, multiple successive frames are stored in cine memory at the acoustic frame rate in response to occurrence of a predetermined characteristic in the cardiac cycle waveform.

Regardless of which frame acquisition mode is employed, the source data volume is formed by retrieving from cine memory the pixel data corresponding to a region of interest in each frame and then processing the pixel data to acquire only pixel data having a velocity or power component lying within a predetermined threshold range, e.g., a non-zero component. This information is then projected onto various imaging planes to reconstruct projected velocity or power images for display.

Velocity or power images are collected in cine memory on a continuous basis. As the probe is swept over an area of the anatomy either by free-hand scanning or using a system for moving the probe, a three-dimensional volume may be obtained. The position of each image with respect to the next may be determined in a number of ways. The probe may be scanned in a manner such as by linear motion, by rocking through an angle, by rotating through an angle perpendicular to the probe face, etc. If the probe is translated at a constant rate, over a known distance or through a known range of angles, the distance between each image can easily be determined. The distance the probe is translated may be determined in a number of ways, such as by simply measuring the distance with a suitable measurement device, using markers on or within the anatomy, or by attaching position sensors to the probe. The probe may also be moved through an arbitrary path and the data from position sensors mounted on the probe may be used to determine the location of each image. These images may then be placed on a Cartesian volume. Alternatively, the probe may be fixed in a device which moves the probe through a known path.

While only certain preferred features of the invention have been illustrated and described, many modifications and changes will occur to those skilled in the art. It is, therefore, to be understood that the appended claims are intended to cover all such modifications and changes as fall within the true spirit of the invention.

What is claimed is:

1. A system for three-dimensional imaging of an object volume containing moving ultrasound scatterers, comprising:
   an ultrasound transducer array for transmitting ultrasound beams and detecting ultrasound echoes reflected from said object volume at a multiplicity of sample volumes;
   means for acquiring imaging data derived at least in part from ultrasound echoes reflected by the ultrasound scatterers, each imaging datum corresponding to a respective one of said multiplicity of sample volumes;
   a scan converter for storing imaging data for each of said multiplicity of sample volumes;
   a computer for retrieving a source imaging data set from the imaging data stored in said scan converter and for projecting average imaging data computed from the imaging data in said source imaging data set onto an image plane so as to form a projected average imaging data set;
   a display monitor; and
   a video processor for displaying a projected image on said display monitor, said projected image being a function of at least a portion of said projected average imaging data set.

2. The system as defined in claim 1 including a cine memory for storing frames of data received from said scan converter, and wherein said computer comprises a three dimensional memory for storing slice data received from said cine memory.

3. A system for three-dimensional imaging of an object volume containing moving ultrasound scatterers, comprising:
   an ultrasound transducer array for transmitting ultrasound beams and detecting ultrasound echoes reflected from said object volume at a multiplicity of sample volumes;
   means for acquiring imaging data derived at least in part from ultrasound echoes reflected by the ultrasound scatterers, each imaging datum corresponding to a respective one of said multiplicity of sample volumes;
   a scan converter for storing imaging data for each of said multiplicity of sample volumes;
   a computer for retrieving a source imaging data set from the imaging data stored in said scan converter and for projecting median imaging data discriminated from the imaging data in said source imaging data set onto an image plane so as to form a projected median imaging data set;
   a display monitor; and
   a video processor for displaying a projected image on said display monitor, said projected image being a function of at least a portion of said projected median imaging data set.

4. The system as defined in claim 3 including a cine memory for storing frames of data received from said scan converter, and wherein said computer comprises a three dimensional memory for storing slice data received from said cine memory.

5. A method for three-dimensional imaging of an object volume containing moving ultrasound scatterers, comprising the steps of:
   transmitting ultrasound beams into said object volume;
   detecting ultrasound echoes reflected from said object volume at a multiplicity of sample volumes;
   acquiring imaging data derived at least in part from ultrasound echoes reflected by the ultrasound scatterers, each imaging datum corresponding to a respective one of said multiplicity of sample volumes;
   storing imaging data for each of said multiplicity of sample volumes;
   retrieving a source imaging data set from the stored imaging data;
   projecting average imaging data computed from the retrieved source imaging data set onto an image plane, thereby forming a projected average imaging data set; and
   displaying a projected image which is a function of a projected imaging data set and which, in turn, comprises at least a portion of said projected average imaging data set.

6. The method as defined in claim 5, wherein said imaging data are velocity data.

7. The method as defined in claim 5, wherein said imaging data are power data.

8. The method as defined in claim 7, wherein the step of projecting average imaging data comprises:
   assigning respective imaging data values to respective points along a cast ray impinging on a pixel in an image plane, each of said points representing a respective intersection of the cast ray with a respective scan plane;
   comparing each one of said respective imaging data values with a predetermined noise threshold;
   accumulating a first string of successive imaging data values not less than said predetermined noise threshold; and
   in response to a next imaging data value following said first string of successive imaging data values, computing as a first average value the average value of said first string of successive imaging data values.

9. The method as defined in claim 8, wherein the step of projecting average imaging data further comprises storing said first average value as part of said projected average imaging data set.

10. The method as defined in claim 8, wherein the step of projecting average imaging data further comprises:
    accumulating a second string of successive imaging data values not less than said predetermined noise threshold; and
    in response to a next imaging data value following said second string of successive imaging data values, computing as a second average value the average value of said second string of successive imaging data values.

11. The method as defined in claim 10, wherein the step of projecting average imaging data further comprises storing the greater of said first and second average values as part of said projected average imaging data set.

12. The method as defined in claim 10, wherein the step of projecting average imaging data further comprises storing the lesser of said first and second average values as part of said projected average imaging data set.

13. The method as defined in claim 8, wherein the number of successive imaging data values included in said first string satisfies a predetermined valid data criterion.

14. The method as defined in claim 5, further comprising the step of projecting median imaging data discriminated from the imaging data in said source imaging data set onto said image plane so as to form a projected median imaging data set that comprises a portion of said projected median imaging data set.

15. The method as defined in claim 8, further comprising the steps of:

assigning respective imaging data values to respective points along a cast ray impinging on a pixel in an image plane, each of said points representing a respective intersection of the cast ray with a respective scan plane;

comparing each one of said repective imaging data values with a predetermined noise threshold;

accumulating a first string of successive imaging data values no less that said predetermined noise threshold;

storing said first string of successive imaging data values in an order sequence of increasing magnitude; and in response to the next imaging data value following said first string of successive imaging data values, discriminating a median value of said first string of successive imaging data values.

16. The method as defined in claim 15, further comprising the step of storing the greater of said first average value and said median value as part of said projected imaging data set.

17. The method as defined in claim 15, further comprising the step of storing the lesser of said first average value and said median value as part of said projected imaging data set.

18. A method for three-dimensional imaging of an object volume containing moving ultrasound scatterers, comprising the steps of:

transmitting ultrasound beams into said object volume;

detecting ultrasound echoes reflected from said object volume at a multiplicity of sample volumes;

acquiring imaging data derived at least in part from ultrasound echoes reflected by the ultrasound scatterers, each imaging datum corresponding to a respective one of said multiplicity of sample volumes;

storing imaging data for each of said multiplicity of sample volumes;

retrieving a source imaging data set from the stored imaging data;

projecting median imaging data discriminated from the retrieved source imaging data set onto an image plane, thereby forming a projected median imaging data set; and displaying a projected image which is a function of said projected median imaging data set.

19. The method as defined in claim 18, wherein said imaging data are velocity data.

20. The method as defined in claim 18, wherein said imaging data are power data.

21. The method as defined in claim 20, wherein the step of projecting median imaging data comprises:

assigning respective imaging data values to respective points along a cast ray impinging on a pixel in an image plane, each of said points representing a respective intersection of the cast ray with a respective scan plane;

comparing each one of said respective imaging data values with a predetermined noise threshold;

storing a first string of successive imaging data values not less than said predetermined noise threshold in an order sequence of increasing magnitude; and in response to a next imaging data value following said first string of successive imaging data values, discriminating as a first median value the median value of said first string of successive imaging data values.

22. The method as defined in claim 21, wherein the step of projecting median imaging data further comprises the step of storing said first median value as part of said projected median imaging data set.

23. The method as defined in claim 21, wherein the step of projecting median imaging data further comprises the steps of:

storing a second string of successive imaging data values not less than said predetermined noise threshold in an order sequence of increasing magnitude; and in response to a next imaging data value following said second string of successive imaging data values, discriminating as a second median value the median value of said second string of successive imaging data values.

24. The method as defined in claim 23, wherein the step of projecting median imaging data further comprises storing the greater of said first and second median values as part of said projected median imaging data set.

25. The method as defined in claim 23, wherein the step of projecting median imaging data further comprises storing the lesser of said first and second values as part of said projected median imaging data set.

26. The method as defined in claim 21, wherein the number of successive imaging data values included in said first string satisfies a predetermined valid data criterion.

* * * * *